(12) United States Patent
Bake (10) Patent No.: US 9,888,931 B2
(45) Date of Patent: Feb. 13, 2018

(54) GUIDE TOOL FOR BONE AND/OR CARTILAGE REPAIR OR JOINT REMODELING

(71) Applicant: EPISURF IP-MANAGEMENT AB, Stockholm (SE)

(72) Inventor: Nina Bake, Stockholm (SE)

(73) Assignee: EPISURF IP-MANAGEMENT AB, Stockholm (SE)

( * ) Notice: Subject to any disclaimer, the term of this patent is extended or adjusted under 35 U.S.C. 154(b) by 4 days.

(21) Appl. No.: 14/901,453

(22) PCT Filed: Jun. 26, 2014

(86) PCT No.: PCT/EP2014/063607
§ 371 (c)(1),
(2) Date: Dec. 28, 2015

(87) PCT Pub. No.: WO2014/207151
PCT Pub. Date: Dec. 31, 2014

(65) Prior Publication Data
US 2016/0199075 A1 Jul. 14, 2016

(30) Foreign Application Priority Data
Jun. 28, 2013 (WO) ................. PCT/EP2013/063707

(51) Int. Cl.
*A61B 17/17* (2006.01)
*A61F 2/42* (2006.01)
(Continued)

(52) U.S. Cl.
CPC ........ *A61B 17/1739* (2013.01); *A61F 2/4225* (2013.01); *A61F 2/4241* (2013.01);
(Continued)

(58) Field of Classification Search
CPC .............. A61B 17/1739; A61B 17/175; A61B 17/1753; A61B 17/1764; A61B 17/1775; A61B 17/1782
(Continued)

(56) References Cited

U.S. PATENT DOCUMENTS 3,765,034 A * 10/1973 Johnston ............ A61B 17/1753
606/98
8,444,651 B2 * 5/2013 Kunz .................. A61B 17/175
606/87
(Continued)

FOREIGN PATENT DOCUMENTS

EP 2389899 A1 11/2011
EP 2389904 A1 11/2011
(Continued)

*Primary Examiner* — Christian Sevilla
*Assistant Examiner* — Eric S Gibson
(74) *Attorney, Agent, or Firm* — Drinker Biddle & Reath LLP (57) ABSTRACT

A guide tool for guiding surgical instrumentation and facilitating insertion of surgical implants for repair of cartilage and/or bone damage and/or for remodeling of a joint surface for improved mobility in a finger or toe joint is disclosed. The guide tool includes an attachment part including a patient specific contact surface adapted to fit the proximal phalanxes or metatarsal bones in a toe or the distal-, middle-, or proximal phalanxes or metacarpal bones in a finger and further including a directing flange. A design model designing a guide tool described above and the use of the instruments are also disclosed.

17 Claims, 9 Drawing Sheets

(51) Int. Cl.
  *A61F 2/46* (2006.01)
  *A61F 2/30* (2006.01)
  *A61B 17/56* (2006.01)

(52) U.S. Cl.
  CPC ........ *A61F 2/4606* (2013.01); *A61B 17/1775* (2016.11); *A61B 17/1782* (2016.11); *A61B 17/562* (2013.01); *A61F 2/30942* (2013.01); *A61F 2002/4228* (2013.01); *A61F 2002/4248* (2013.01); *A61F 2002/4251* (2013.01); *A61F 2002/4687* (2013.01)

(58) Field of Classification Search
  USPC .............................................. 606/86–89, 96
  See application file for complete search history.

(56) References Cited

U.S. PATENT DOCUMENTS

| | | | | |
|---|---|---|---|---|
| 8,623,026 | B2* | 1/2014 | Wong | A61B 17/1703 29/592 |
| 8,644,973 | B2* | 2/2014 | Bake | A61F 2/30756 606/88 |
| 8,655,468 | B2* | 2/2014 | Bake | A61B 17/1675 606/86 |
| 8,657,822 | B2* | 2/2014 | Bake | A61F 2/30756 606/80 |
| 8,734,455 | B2* | 5/2014 | Park | A61B 17/175 606/89 |
| 8,939,982 | B2* | 1/2015 | Chellaoui | A61B 17/157 606/86 B |
| 9,113,971 | B2* | 8/2015 | Metzger | A61B 17/175 |
| 9,173,661 | B2* | 11/2015 | Metzger | A61B 17/15 |
| 9,351,744 | B2* | 5/2016 | Kunz | A61B 17/1721 |
| 9,386,993 | B2* | 7/2016 | Meridew | A61B 17/15 |
| 9,408,616 | B2* | 8/2016 | Kehres | A61B 17/15 |
| 9,408,618 | B2* | 8/2016 | Park | A61B 17/175 |
| 9,439,678 | B2* | 9/2016 | Bake | A61B 17/1764 |
| 9,474,539 | B2* | 10/2016 | Catanzarite | A61B 17/155 |
| 9,480,490 | B2* | 11/2016 | Metzger | A61B 17/1764 |
| 9,522,010 | B2* | 12/2016 | Metzger | A61B 17/157 |
| 9,539,013 | B2* | 1/2017 | Katrana | A61B 17/15 |
| 9,561,041 | B2* | 2/2017 | Snider | A61B 17/175 |
| 2008/0287954 | A1* | 11/2008 | Kunz | A61B 17/175 606/87 |
| 2009/0018546 | A1* | 1/2009 | Daley | A61B 17/175 606/92 |
| 2009/0118736 | A1* | 5/2009 | Kreuzer | A61B 17/175 606/96 |
| 2009/0222015 | A1* | 9/2009 | Park | A61B 17/175 606/89 |
| 2009/0222016 | A1* | 9/2009 | Park | A61B 17/175 606/89 |
| 2009/0228048 | A1* | 9/2009 | Duncan | A61B 17/1782 606/286 |
| 2009/0254093 | A1* | 10/2009 | White | A61B 17/175 606/89 |
| 2010/0087829 | A1* | 4/2010 | Metzger | A61B 17/15 606/96 |
| 2010/0121325 | A1* | 5/2010 | Tyber | A61B 17/1717 606/62 |
| 2010/0168866 | A1* | 7/2010 | Shih | A61B 17/1604 623/23.14 |
| 2010/0286700 | A1* | 11/2010 | Snider | A61B 17/175 606/89 |
| 2011/0015639 | A1* | 1/2011 | Metzger | A61B 17/175 606/91 |
| 2011/0178524 | A1* | 7/2011 | Lawrence | A61B 17/15 606/87 |
| 2012/0010719 | A1* | 1/2012 | Reiley | A61B 17/72 623/21.18 |
| 2012/0041446 | A1* | 2/2012 | Wong | A61B 17/1703 606/96 |
| 2012/0123420 | A1* | 5/2012 | Honiball | A61B 17/1764 606/87 |
| 2012/0130382 | A1* | 5/2012 | Iannotti | A61B 17/15 606/87 |
| 2012/0150186 | A1* | 6/2012 | Hajianpour | A61B 17/171 606/59 |
| 2012/0239045 | A1* | 9/2012 | Li | A61B 17/15 606/88 |
| 2012/0290019 | A1* | 11/2012 | Chellaoui | A61B 17/157 606/86 R |
| 2012/0296339 | A1* | 11/2012 | Iannotti | A61B 17/15 606/87 |
| 2012/0303033 | A1* | 11/2012 | Weiner | A61B 17/151 606/87 |
| 2013/0012952 | A1* | 1/2013 | Fallin | A61B 17/1714 606/96 |
| 2013/0085500 | A1* | 4/2013 | Meridew | A61B 17/15 606/89 |
| 2013/0172891 | A1* | 7/2013 | Bake | A61F 2/30756 606/80 |
| 2013/0173228 | A1* | 7/2013 | Bake | A61F 2/30756 703/1 |
| 2013/0185927 | A1* | 7/2013 | Bake | A61B 17/1675 29/592 |
| 2013/0231668 | A1* | 9/2013 | Olsen | A61B 17/151 606/79 |
| 2014/0094861 | A1* | 4/2014 | Fallin | A61B 17/1775 606/86 R |
| 2014/0142643 | A1* | 5/2014 | Bake | A61B 17/1764 606/86 R |
| 2014/0243836 | A1* | 8/2014 | Bake | A61F 2/30756 606/88 |
| 2014/0343403 | A1* | 11/2014 | Kunz | A61B 17/1721 600/424 |
| 2015/0134011 | A1* | 5/2015 | Medoff | A61B 17/1728 606/286 |
| 2015/0320430 | A1* | 11/2015 | Kehres | A61B 17/15 606/87 |
| 2016/0030183 | A1* | 2/2016 | Bake | A61F 2/30942 606/86 R |
| 2016/0038160 | A1* | 2/2016 | Metzger | A61B 34/10 606/86 R |
| 2016/0100848 | A1* | 4/2016 | Lin | A61B 17/1739 606/87 |
| 2016/0151076 | A1* | 6/2016 | Bake | A61F 2/28 606/80 |
| 2016/0199075 | A1* | 7/2016 | Bake | A61F 2/46 606/96 |
| 2016/0310217 | A1* | 10/2016 | Park | A61B 17/175 |
| 2016/0324532 | A1* | 11/2016 | Montoya | A61B 17/151 |

FOREIGN PATENT DOCUMENTS

| | | | |
|---|---|---|---|
| EP | 2564792 A1 | 3/2013 | |
| WO | WO 2008138137 A1 * | 11/2008 | ........ A61B 17/175 |
| WO | WO 2011147837 A1 * | 12/2011 | |
| WO | WO 2013030370 A1 * | 3/2013 | |

* cited by examiner

GUIDE TOOL FOR BONE AND/OR CARTILAGE REPAIR OR JOINT REMODELING

CROSS-REFERENCE TO PRIOR APPLICATION

This application is a §371 National Stage Application of PCT International Application No. PCT/EP2014/063607 filed Jun. 26, 2014, which claims priority to International Application No. PCT/EP2013/063707 filed on Jun. 28, 2013, both of which are incorporated herein in their entirety.

FIELD OF THE INVENTION

This invention relates in general to the field of orthopedic surgery and to guide tools for use during orthopedic surgery. More particularly the present invention relates to guide tools and/or insert tools and/or implants for replacement of damaged cartilage and/or bone at a joint surface in a toe or a finger and/or for remodeling of a joint surface.

BACKGROUND

General Background

Pain and overuse disorders of the joints of the body is a common problem. Pain in the toe can be caused by for example injury, arthritis or infection. One example of a common problem of arthritis in the toe is the syndrome "stiff big toe" or Hallux rigidus, which is arthritis in the first metatarsophalangeal joint (MTP) in the big toe, consisting of the distal part of the first metatarsal bone and the proximal part of the proximal phalanx of the big toe (hallux) making the joint stiff.

Hallux rigidus is the second most common form of disability in the first metatarsophalangeal (MTP) joint, where the most prominent and perhaps more renown disease is hallux valgus. Davis-Colley was the first to describe the disease in 1887 as a "flexed plantar position of the proximal phalanx of the hallux relative to the metatarsal head". He first named the disease hallux flexus, but has since then been given a multitude of names over the years; hallux rigidus, hallux limitus, dorsal bunion, hallux dolorosus and hallux malleus.

Hallux rigidus is the manifestation of osteoarthritis in the first MTP joint, and is a common disease with an incidence of 2.5% in people older than 50 years of age. The typical age for surgical intervention in patients with hallux rigidus is between 50 and 60 years, and has a slightly higher presence in females. Most cases of hallux rigidus are present bilaterally, although cases have been found to be unilateral especially when correlated with some trauma or injury.

However, 80% of patients who have been monitored for a prolonged period of time develop bilateral symptoms. In addition, about 95% of cases with a positive family history of a hallux pathology present bilateral hallux rigidus, and 80% of patients with hallux rigidus have a positive family history. This might be because the shapes of the metatarsophalangeal joint can in itself produce stiffness in the joint, as acongenitally flat, square or chevron-shaped metatarsal head will influence the movement in the joint.

Many different surgical interventions can be found in the literature, advisable at different severity levels. There are some purely conservative treatments (rest, anti-inflammatory drugs, insoles etc.) in the earlier stages of the progression, although most treatments are eminently surgical. The surgical interventions range from osteotomies (early stages), arthrodesis (late stages) or other means of arthroplasty.

The weight-bearing and articulating surfaces of the toe, and of other joints, are covered with a layer of soft tissue that typically comprises a significant amount of hyaline cartilage. The friction between the cartilage and the surrounding parts of the joint is very low, which facilitates movement of the joints under high pressure. The cartilage is however prone to damage due to disease, injury or chronic wear. Moreover it does not readily heal after damages, as opposed to other connective tissue, and if healed the durable hyaline cartilage is often replaced by less durable fibrocartilage. This means that damages of the cartilage gradually become worse. Along with injury/disease comes a problem with pain which results in handicap and loss of function. It is therefore important to have efficient means and methods for repairing bone and/or cartilage defects in toe and finger joints.

Specific Background

Toe and finger joints are unique in their shape and form and are quite small in comparison to other joints in the body and there is a need for tools and methods for repair of damaged bone and/or cartilage in toe and finger joints. Current methods comprise using two implants or larger implants. There is a need for a method and tools for replacing cartilage and/or bone damages in a toe or a finger by insertion of implants by using minimally invasive surgery (MIS) or new method or tools for remodeling of a joint surface.

PRIOR ART

Examples of prior art for repair tools for toe joints include the insertion of a larger implants in toe or finger joints and most involve repair of both of the bone parts that meet in the joint to be repaired.

FIGURES

FIGS. 7A and 7B show an exemplifying embodiment of the guide tool according to the invention comprising a reamer guide surface in two different angles, FIG. 7A is from a side view and FIG. 7B from above.

OBJECT OF THE INVENTION

The guide tool and/or insert tools and/or implants according to the invention are designed to achieve stable and secure placement in a joint in order to assist replacement of a part of the bone and/or cartilage in a joint during surgery. The secure placement of the guide tool according to the invention and the "easy to use" guide tool according to the invention makes the surgery more precise and less surgeon dependent since the placement of the guide is self-instructive and the guide also assists to keep away surrounding tissue from the site of surgery which facilitates for the surgeon.

Objects of the present invention are;
to facilitate surgery for the surgeon,
make the surgery safer and also achieve more precise and durable results of repair of the joint.
Other objects of the invention are;
to make the surgery cheaper and faster due to improved tools.
Another object of the invention is;
to achieve less- or minimally invasive surgery which allows for less interference in the surrounding tissue

SUMMARY

The present invention relates in general to the field of orthopedic surgery and to guide tools for use during orthopedic surgery. More particularly the present invention relates to guide tools and/or insert tools and/or implants for replacement of damaged cartilage and/or bone at a joint surface in a toe or a finger and/or for remodeling of a joint surface.

The present invention relates to a guide tool 1 for guiding surgical instrumentation and facilitating insertion of surgical implants for repair of cartilage and/or bone damage and/or for remodeling of a joint surface for improved mobility in a finger or toe joint wherein said guide tool 1 comprises;
an attachment part 5 comprising a patient specific contact surface 51 adapted to fit of the proximal phalanxes or metatarsal bones in a toe or the distal-, middle-, or proximal phalanxes or metacarpal bones in a finger.

A first aspect of the invention is a guide tool 1 for secure positioning according to claim 1 comprising an attachment part 5 comprising a patient specific contact surface 51 which is further adapted to correspond to a part of the contour and shape of a joint surface of the diaphysis or long shaft part of the proximal phalanxes or metatarsal bones in a toe or the distal-, middle-, or proximal phalanxes or metacarpal bones in a finger.

Said guide tool is further secured by a directing flange 25 on a second patient specific contact surface 51', placed opposite the first patient specific contact surface 51 and wherein said second area of the patient specific contact surface 51' is adapted to correspond to the surface of the epiphysis.

Said flange may be as a small protrusion of irregular shape or any other suitable shape such as half circular. The flange gives support in placement of the guide and gives improved stability of the guide.

Further aspects of the invention are;
a guide tool 1 for secure positioning according to the claims comprising an attachment part 5 further comprising one area of a patient specific contact surface 51 an 51', which are adapted to correspond to the bone surface of the diaphysis which is the long shaft part of the proximal phalanxes or metatarsal bones in a toe or the distal-, middle-, or proximal phalanxes or metacarpal bones in a finger in combination with comprising another area of a second patient specific contact surface 51' comprised in the structure of the guide device part 3 and/or comprised in the directing flange 25 structure of the guide tool and wherein said second area of the patient specific contact surface 51' is adapted to correspond to the surface of the epiphysis which is an expanded portion of the proximal phalanxes or metatarsal bones in a toe or the distal-, middle-, or proximal phalanxes or metacarpal bones in a finger.

A guide tool 1 for secure positioning according to the invention further comprising an opening comprised in the guiding device part 3 of the guide tool 1.

A guide tool 1 for secure positioning according to the invention further comprising one or more attachment devices 7.

A guide tool 1 for secure positioning according to the invention made of materials approved for medical procedures selected from ceramic, plastic, polymer or metal material.

A guide tool 1 for secure positioning according to the invention, wherein the guiding device part 3 comprises an opening 11 facing the part of the joint which has a joint damage.

A guide tool 1 for secure positioning according to the invention, wherein the directing flange 25 is comprised of a body which is a protuberance and comprised in the same structure as the guiding device part 3.

A guide tool 1 for secure positioning according the invention further comprising a directing flange 25 which is pointing in a direction so that it encloses the shape of the bone and/or cartilage in a toe or finger joint and which may comprise a part of the first 51 or second 51' patient specific contact surface.

A guide tool 1 for secure positioning according the invention comprising a directing flange 25 having a small protrusion of irregular shape or any other suitable shape such half circular giving support in the placement of the guide and improved stability of the guide.

A guide tool 1 for secure positioning according to the invention further comprising an opening 11 which is formed so that it follows or matches the shape of the joint surface beneath making the placement of the guide tool 1 robust and easy (indicating desired placement to the surgeon) and making the guide tool 1 less prone to move during surgery.

Another aspect of the invention is a design method designing said guide tool and or implant and or insert tools according to the present invention wherein the method comprises the steps of;
collecting input data selected from Surgical preference data 104, image data 106, demographic parameters 108, model information 110, implant design options 112, instrument design options 114 and consider all data and transfer the data to form a decision process 120;

Using the decision process to make output data comprising of shape and design of guide tool 122, shape and design of insert tools 124, shape and design of guide tool patient specific contact surface 126, implant design 128 wherein the method is characterized in;

the step for input data of guide tool always comprise data for designing a patient specific contact surface 51 of a guide tool 1 adapted to fit the patient specific contact surface of the proximal phalanxes or metatarsal bones in a toe or the distal-, middle-, or proximal phalanxes or metacarpal bones in a finger, and further aspects are;

A design method according to the invention wherein the step for input data of guide tool always comprises designing patient specific contact surface 51 of a guide tool 1 adapted to fit at least a part of the diaphysis or long shaft part of the placement bone.

A design method according to claims 12-14 further comprising any of the features according to the invention.

The present invention also relate to the use of said guide tool and or insert tools and or implant for repair of a joint damage in a joint and/or for remodeling of a joint surface.

The different described varieties of the guide tool, the design method and the use according to the invention may be combined in any way according to the invention.

DETAILED DESCRIPTION

Guide Tool 1

The guide tool 1 according to the invention is designed to achieve stable and secure placement for guiding insert tools for use in a joint in order to replace a part of the bone and/or cartilage in a joint and/or for guiding placement of an implant and/or for remodeling of a joint surface for improved mobility.

The guide tool guide tool 1 according to the invention for guiding surgical instrumentation and facilitating insertion of surgical implants for repair of cartilage and/or bone damage in a finger or toe joints wherein said guide 1 comprises;

an attachment part 5 comprising a patient specific contact surface 51 adapted to fit the surface of the proximal phalanx or metatarsal bones in a toe or the distal-, middle-, or proximal phalanx or metacarpal bones in a finger a guiding device part 3 comprising an opening 11 facing the part of the joint which has a joint damage.

The attachment part 5 has a patient specific contact surface 51 that has a shape and contour that is designed to correspond to and to fit the contour of the cartilage or the bone of at least a part of the placement bone 206 in a predetermined area.

The placement bone 206 according to the present invention is a proximal phalanx or metatarsal bones in a toe or the distal-, middle-, or proximal phalanx or metacarpal bones in a finger, for example bones in the thumb (pollex). For example, suitable attachment area for the a patient specific contact surface 51 to correspond to is to the shape and contour of is the part of the placement bone 206 which is conformed as a long shaft, for example the diaphysis. In some cases the second patient specific contact surface 51' is conformed to also correspond to parts of the expanded portion of the bones, the epiphysis of the proximal phalanx or metatarsal bones in a toe or the distal-, middle-, or proximal phalanx or metacarpal bones in a finger in a hand.

The attachment part 5 also has a second surface 314 opposite to the cartilage contacting surface 51. The guiding device part 3 extends from said second surface 314 of the attachment part 5. See for example in FIG. 4.

The guide tool 1 is easy to place due to the precise fit of the attachment part 5 on the surface of parts of the placement bone 206. The guide tool 1 is designed to be inserted in as small lesion as possible to be able to repair the specific cartilage damage.

The size and shape of patient specific contact surfaces 51 and 51' of the guide tool 12 is determined depending on the size and shape of the part of the placement bone 206 which is selected for anchoring and support for the guide tool 1. The size and shape of the patient specific contact surface 51 and 51' is a consideration between the following aspects; minimize surgery lesion, maximize stability for guide tool 11, anatomic limitations on the site of the injury. A large size of the patient specific contact surfaces 51 and 51' is always to prefer to get good stability of the guide tool, however, a large surface area of the surface 51 also leads to a large surgical intervention and this is not preferred. Preferably the patient specific contact surface 51 covers a part of the diaphysis of the placement bone 206.

The patient specific contact surface 51 may be several cartilage contact areas which are spread out and are chosen to correspond to different locations on the placement bone 206. For example a patient specific contact surface 51 may have one area or field which corresponds to a diaphysis part of the placement bone 206 and another area or field that corresponds to an epiphysis part of the placement bone. These two fields or areas may be a continuous surface or may be separated fields or areas but are still referred to as the patient specific contact surface 51.

The size of the patient specific contact surface 51 and of the guiding device part 3 are determined by a balance between the desire to achieve good positioning stability and the desire to achieve minimally invasive surgery.

When designing the guide tool, the patient specific contact surface 51 can be designed to comprise three points distributed over the surface of the joint where the implant is to be inserted. The points are spread out over an area and chosen to give maximum support and positional stability for the guide tool 1 during surgery and thus these points, either decided and identified by the surgeon or automatically identified by design software, serve the ground when designing the patient specific contact surface 51 of the guide tool 1. The patient specific contact surface 51 can also be formed such that it uses the curvature in the surface in a joint for stability without other attachment devises. Optionally the attachment part 5 comprising the cartilage contacting surface 51 can be further stabilized by attachment with nails, rivets or similar attachment means 9 to the bone surrounding the cartilage in a joint (see for example FIG. 4). This additional attachment with rivets or the like gives additional support and stability and also gives the possibility to keep the patient specific contact surface as small as possible. The guide tool may further comprise one or several attachment devices (7). The attachment devices may be premade recesses or just visible marks suitable for attachment of for example rivets or pins.

The guide-tool 1 aids with exact precision removal of a volume of cartilage and subchondral bone 416 (see FIG. 8 for example of a bone and/or cartilage part which can be removed using the guide tool according to the invention) and the guide tool 1 also may guide the placement of the implant 10 in for example a toe or a finger joint. Placement of the guide-tool 1 on the surface in a joint can for example be seen in FIG. 4, using a guide further comprising a guide channel 54.

The guide tool 1 is manufactured using a suitable material or materials that is/are approved for use in medical procedures, e.g. a ceramic, plastic or aluminia material. The guide tool 1, especially the patient specific contact surface 51, is also preferably made of a material that is smooth, even and/or has low friction, in order to lessen the risk of wear and damage to the cartilage on which it is to be placed.

Attachment Part 5 of the Guide Tool 1

The attachment part 5 of the present invention has a surface which is adapted to achieve secure attachment of the guide tool 1 to the bone. The attachment part 5 comprises the patient specific contact surface 51 which is designed to correlate to a surface of the proximal phalanx or metatarsal bones in a toe or the distal-, middle-, or proximal phalanx or metacarpal bones in a finger of a patient.

The attachment part 5 may comprise one or several attachment devices 7. In one embodiment the attachment part 5 comprises recesses for anchoring of the attachment part into the bone with pins 9 or other suitable attachment devises. In one embodiment the precise fit of the patient specific contact surface 51 of the attachment part 5 is enough to achieve stability for the guide tool during surgery. The attachment part 5 is attached to the placement bone 206 which is a bone part selected from the proximal phalanx or metatarsal bones in a toe or the distal-, middle-, or proximal phalanx or metacarpal bones in a finger of a patient.

In other embodiments the attachment part 5 are attached to the placement bone 206 using pins 9. For example in FIG. 1*a-b* the attachment part 5 is attached to the placement bone 206 using two pins 9 through two attachment devices 7 which in this embodiment are designed to comprise recesses in the guide tool 1.

Figure 9A:
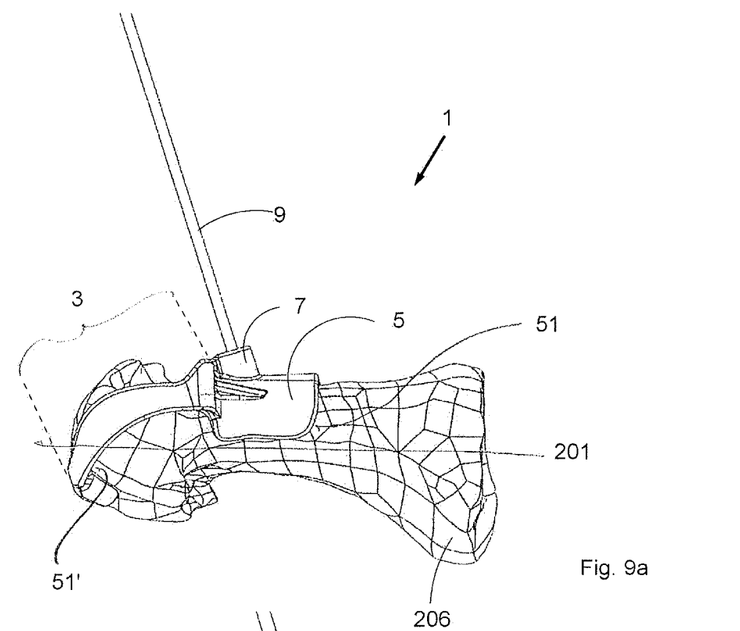
FIG. 9A shows an alternative embodiment of the guide tool from one side.
Figure 9B:
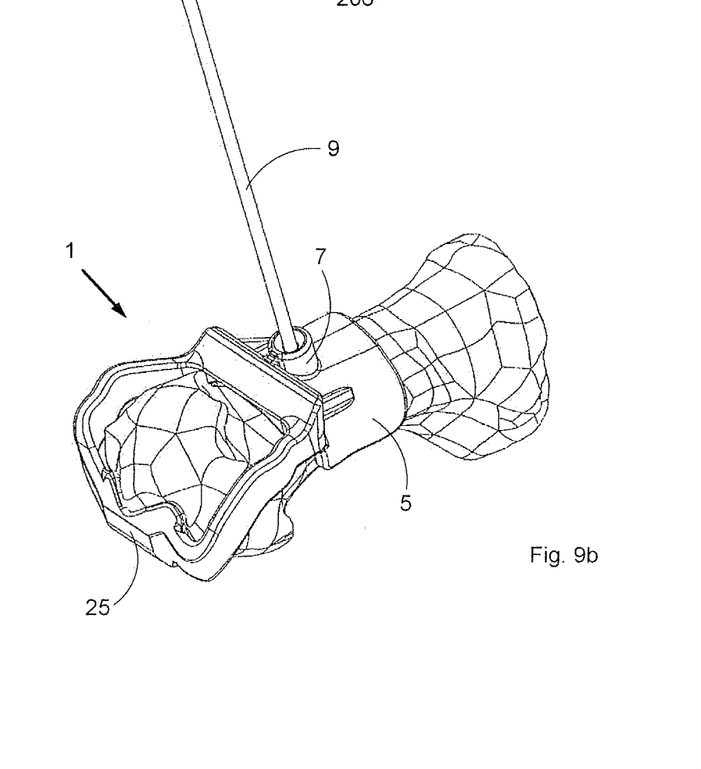
FIG. 9B shows alternative embodiment of the guide tool from above and one side.

In the guide tool illustrated in FIGS. 9A and 9B only one pin 9 is fitted through the attachment device 7.

Patient Specific Contact Surfaces 51 and 51' of the Guide Tool 1

The patient specific contact surface 51 is designed to correlate and/or corresponds to the curvature of at least a part of the surface of the proximal phalanx or metatarsal bones in a toe or the distal-, middle-, or proximal phalanx or metacarpal bones in a finger of a patient.

The guide tool 1 may comprise several patient specific contact surfaces 51 and 51' correlating to additional areas of the joint other than the one area of the surface of the proximal phalanx or metatarsal bones in a toe or the distal-, middle-, or proximal phalanx or metacarpal bones in a finger of a patient. See for example in FIG. 7B an example wherein the patient specific contact surface 51 is two separated areas (comprised in the attachment part 5 and in the guide device part 3, illustrated with a grid pattern (surface 51) in the FIG. 7B and abutting the bone and/or cartilage structures. Another example is found in FIGS. 1A and 1B, wherein the patient specific contact surface 51 also is two separated areas (comprised in the attachment part 5 and in the guide device part 3, illustrated with a grid pattern (surface 51) in the FIG. 7B and abutting the bone and/or cartilage structures.

Figure 4:
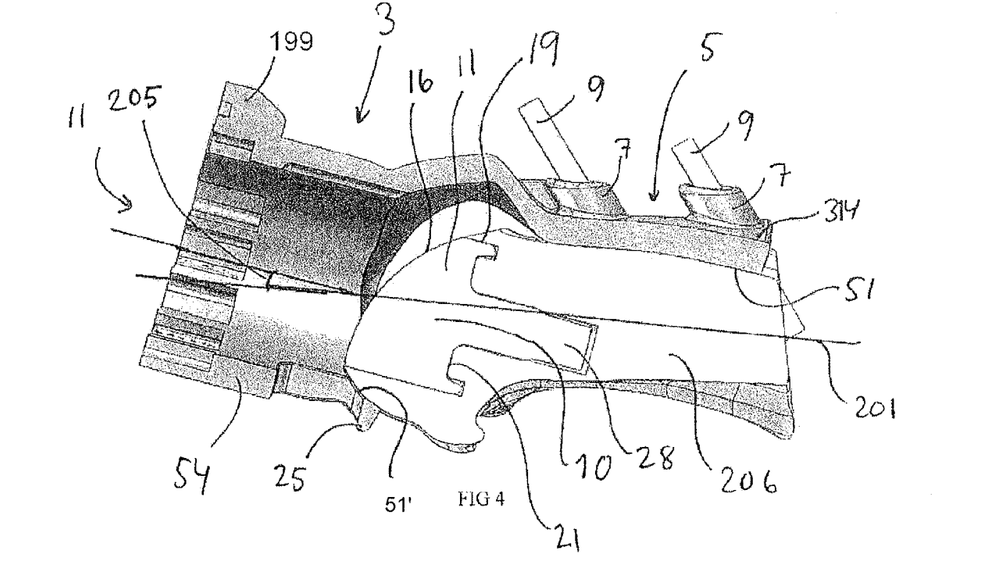
FIG. 4 shows an exemplifying embodiment of the guide tool in a cross sectional view according to the invention wherein the guide tool is placed in a joint and wherein the guiding device part comprises a guide channel and the position of the inserted implant in the joint is shown in cross section.

The patient specific contact surface 51 and 51' of the guide tool 1, which can be found in FIG. 4 and FIG. 9A may also further comprise a patient specific contact surface 51 which is located both on the guiding device part 3 as 51' and the attachment part 5 as 51, which further supports the guide tool 1 and the guiding device part 3 of the guide tool 1 during surgery.

The patient specific contact surface may be designed to correspond to a cartilage or joint surface in a specific patient (individually designed) or to correspond to general information about a joint surface of a toe or finger.

The patient specific contact surface 51 is conformed so that it uses the topography of the joint in order to prohibit rotation of the guide tool, or movement of the guide tool once the guide tool is placed in the surgical site.

The opening 11 may be formed so that it follows or matches the shape of the joint surface beneath making the placement robust and easy (indicating desired placement to the surgeon) and making the guide less prone to move during surgery.

Directing Flange 25 of the Guide Tool 1

Figure 1A:
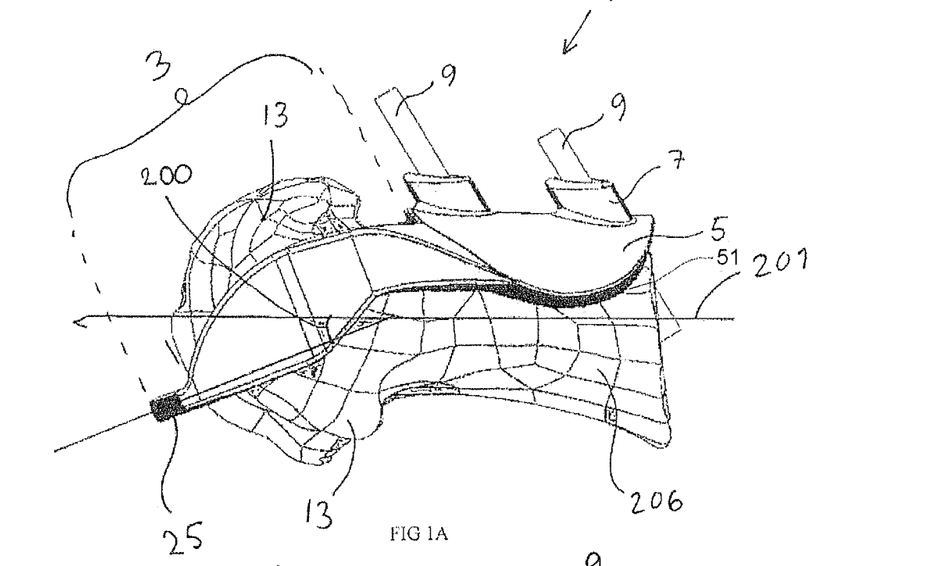
FIGS. 1A and 1B show an exemplifying embodiment of the guide tool according to the invention in two different angles, from one side in FIG. 1A and from above and from one side in FIG. 1B.
Figure 2A:
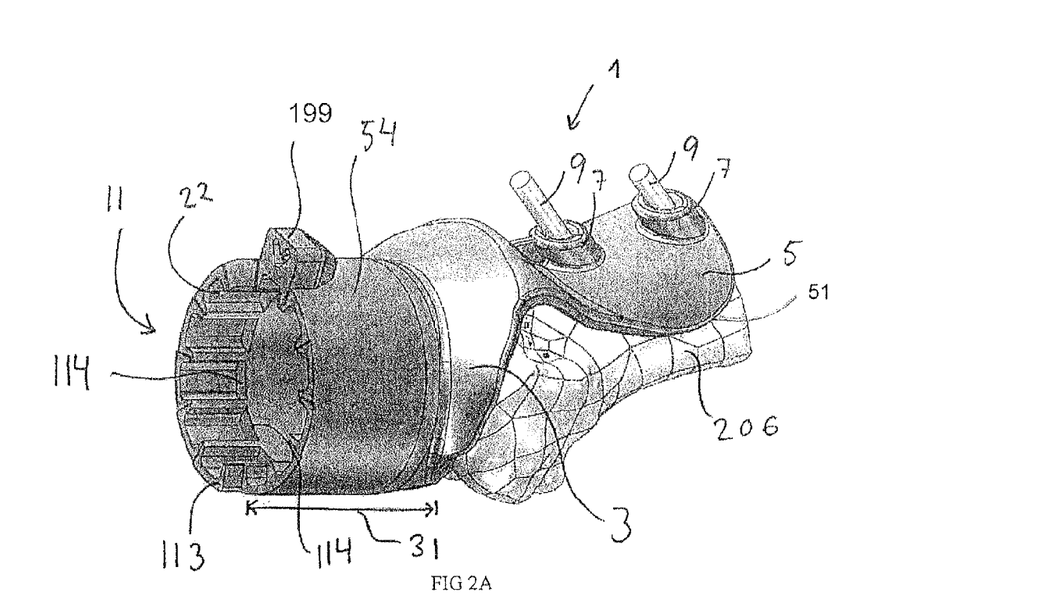
FIGS. 2A and 2B show an exemplifying embodiment of the guide tool according to the invention in two different angles, from one side in FIG. 2B and from above and from one side in FIG. 2A, wherein the guiding device part comprises a guide channel.
Figure 2B:
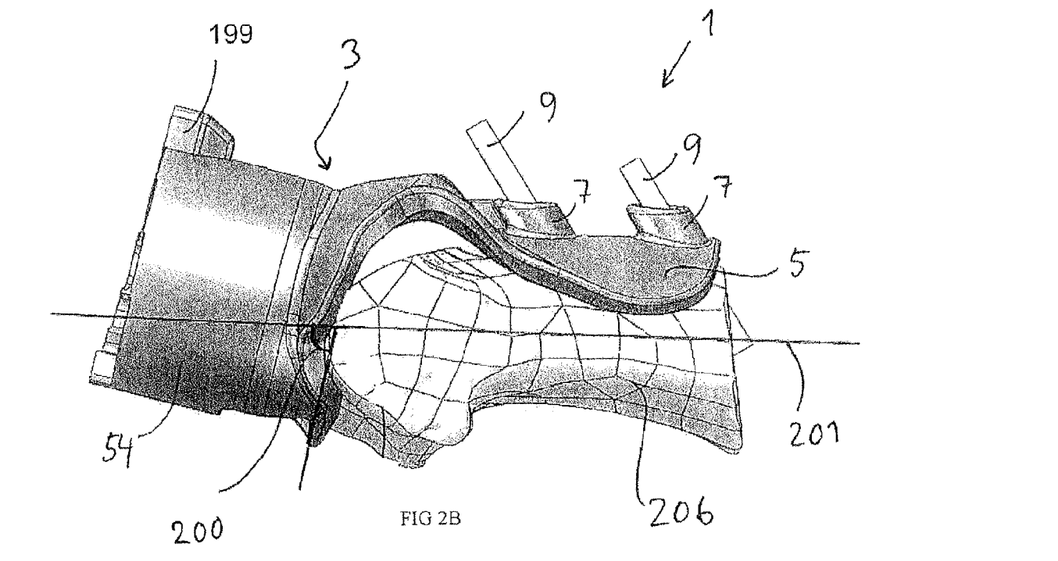

The guide tool 1 according to the invention comprises a directing flange 25, see for example FIG. 1A and FIG. 2B. The directing flange 25 is comprised of a body which is a protuberance of the guiding device part 3 and it is pointing in such a direction that it encloses the shape of the bone and/or cartilage in a patient. Alternatively the flange is formed as a small protrusion of irregular shape or any other suitable shape such as half circular illustrated in FIG. 9B. The flange gives support in placement of the guide and gives improved stability of the guide.

The purpose of the directing flange 25 is to guide the placement of the guide in the surgical site and thereby make the placement of the guide easier for the surgeon. When the guide tool 1 is placed in the joint during surgery the directing flange 25 is positioned so that directing flange 25 encloses the bone structure and this makes the placement of the guide easier, especially guiding the surgeon about the rotational fit compared to the longitudinal bone in the toe or finger joint which is matched by the patient specific contact surface 51 of the attachment part 5. Also, the directing flange 25 for use in combination with the patient specific contact surfaces 51 (which also help the surgeon to know how to place the guide in the surgical site) makes the placement even easier and more precise. These features make the guide to have a specific fit (by itself or in combination) on the bone and/or cartilage surfaces in the joint.

A guide tool 1 according to the invention, comprising the attachment part 5 adapted to correspond to the epiphysis part of any of the bones; proximal phalanx or metatarsal bones in a toe or the distal-, middle-, or proximal phalanx or metacarpal bones in a finger of a patient makes the guide tool easy to use for a surgeon since the surface of the epiphysis part of these bones are often intact and therefore they are suitable to use for attachment of the guide tool. Other areas of the bones in the finger may have had additional growth of cartilage which makes those parts hard to analyze in advance and more difficult to predict by CT or MR imaging or by other techniques.

Different Embodiments of the Guide Tool According to the Invention

The guide tool according to the invention is used during surgery and replacement of damaged cartilage and or bone and/or for remodeling of a joint surface.

In one embodiment according to the invention the guiding device part 3 of the guide tool comprises an opening 11, said opening 11 may further be comprised by a guide channel 54.

The guide channel 54 may be adapted so that insert tools may be used inside the opening 11 of the guide channel 54.

The opening 11 of the guide channel 54 has an inner cross-sectional area that is designed to correspond or to be larger than the cross-sectional area of the articulating first surface 16 of the implant 10 (see FIG. 4). In other words, the plate shaped implant body 10 may fit the guide channel 54, with a slight tolerance to allow a sliding movement of the implant in the guide channel 54 or the implant may be placed in the made bone recess after removal of the guide tool 1. The opening 11 of the guide channel 54 is in a position on the joint surface, approximately comprising the site of the diseased cartilage and or/bone part in a joint. The height 31 of the guide channel 54 must be sufficiently long to give support to the tools used inside the guide channel 54. The height 31 is preferably higher than the thickness of the surrounding tissue. In this way, the opening of the guide channel 54 is easy to access for the surgeon. The height 31 of the guide channel 54 is between 2 and 10 cm and always sufficiently high to ensure stabilization of the tools that are to be inserted into the guide channel 54. The height 31 of the guide channel 54 is sufficiently high to be easily accessible for the surgeon during surgery. In one embodiment, the top opening 11 of the guide channel 54 is designed to project above the tissue surrounding the surgery cut when the guide tool is placed on the cartilage in a joint during surgery.

The height or length 31 of the guide channel 54 must be sufficiently long to give support to the tools used inside the opening 11 of the guide channel 54. The height 31 is preferably higher than the thickness of the surrounding tissue. In this way, the opening 11 of the guide channel 54 is easy to access for the surgeon. The height 31 of the guide channel 54 is between 1 and 10 cm or between 2 and 10 cm and always sufficiently high to ensure stabilization of the tools that are to be inserted into the guide channel 54.

In one embodiment the guide channel comprises means for adjusting reach depth of insert tools used inside the guide channel 54. For example the means for adjusting height may for example adjust how deep a drill bit may reach when the guide tool 1 guides drilling.

In one embodiment the guide channel 54 further comprises a height adjustment device 18 being arranged to enable stepwise adjustment of said length or height 31 of the guide channel 54.

Figure 3:
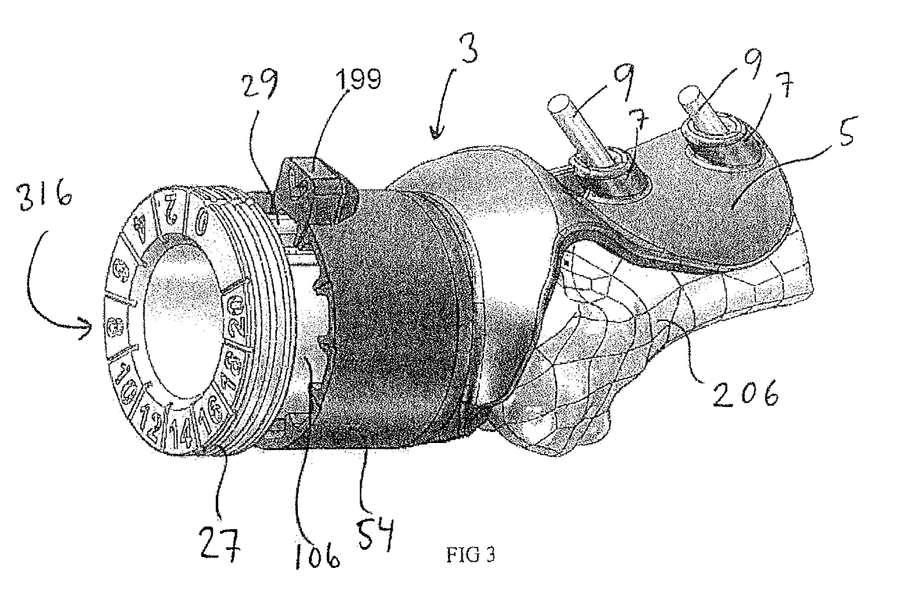
FIG. 3 shows an exemplifying embodiment of the guide tool according to the invention wherein the guiding device part comprises a guide channel which further comprises an insert tool.

The guide tool 1 according to the invention may comprise a height adjustment device 18 that further comprises a female receiving part, which may be a part of the guide channel 54 and or the opening 11 and which comprises an inner surface provided with a plurality of grooves 22, see FIG. 2a, extending from the edge 113 of the upper opening of said female receiving part and wherein the height adjustment device further comprises a male part 27, see FIG. 3, equipped with ridges 29, protruding from an outer surface 106 of the male part 27 allowing for height adjustment of insert tools used inside the male part and wherein the male part also has an opening 316.

A guide tool 1 according to the invention may comprise a height adjustment device 18 wherein the length 31 of the guide channel 54 is adjusted by moving the male part 27 in relation to the female receiving part so that a ridge 29 of the male part is moved from one groove 22 to another groove 22 of the female receiving part.

A guide tool 1 according to the invention may comprise a height adjustment device 18 wherein the stepwise height adjustment is made by steps of 0.01-0.6 mm or for example 0.1-0.3 mm or for example 0.2 mm due to the position of a groove 17 relative to the patient specific contact surface 51.

A guide tool 1 according to the invention may comprise a height adjustment device 18 wherein the male part 27 when placed inside the female part is in a locked position and is not able to rotate due to the placement of the ridge 129 of the male part 27 in the groove 22 of the female receiving part.

A guide tool 1 according to the invention may comprise a height adjustment device 18 wherein the ridges 29 of the male part 27 is moved from one groove 22 to another by lifting the male part outwards from the joint surface and then placing the male part down in another groove 22, and wherein the male part 27 when placed inside the female receiving part is in a locked position and is not able to rotate.

A guide tool 1 according to the invention may comprise a height adjustment device 18 wherein the plurality of grooves 22 extending from the edge 113 of the upper opening 11 of said female receiving part or guide channel 54 and having a cross-section allowing the ridge 29 to enter a groove 22 on the female receiving part and stop against the abutment 114 of said groove 22, see for example FIG. 2a showing a view inside a female receiving part which is a part of the guide channel 54 and also shows grooves 22 and said abutment.

In one embodiment the guide tool 1 comprise a guiding device part 3 which is further comprises a reamer guide surface 23 allowing bone and cartilage which protrudes through the opening 11 which is comprised in the reamer guide surface 23 when the guide tool 1 is placed in the joint. The reamer guide surface 23 allows for the protruding bone and cartilage to be removed in a certain predetermined angle due to the shape and angle of the reamer guide surface and due to the opening 11 of the guiding device part 3 forming a new articulating surface 400 in the joint. See FIG. 7B which shows a joint after the guide tool comprising the reamer surface 23 is used and a part of the joint was removed in a predetermined angle forming a vaulted surface in the joint.

The new surface 400 created by the guide tool comprising may serve as input information for design of the second guide tool and thereby the new surface 400 (or a planned new surface 400) may be used for design of a patient specific contact surface 51 of a second guide tool wherein the patient specific contact surface 51 is constructed to correspond to parts of the new surface 400. See for example FIGS. 7A and 7B, which show the new surface 400

Figure 8:
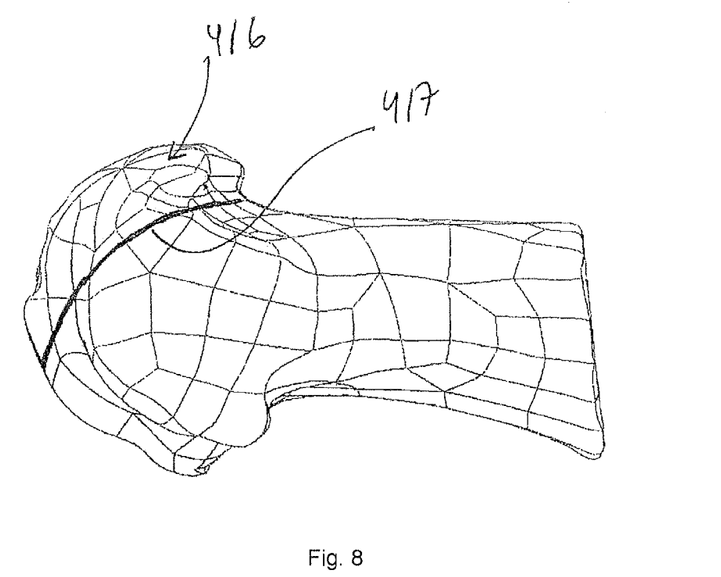
FIG. 8 shows a planned new surface on a bone before surgery.

FIG. 8 shows a mark wherein the guide tool comprising a reamer surface is to be used to remove the marked section 411 in a certain angle 417.

In FIGS. 2A and 2B a guide tool comprising a guide channel 54 is placed in the joint. In FIGS. 2A and 2B an example of a guiding device part 3 which also comprises a patient specific contact surface 51 (not only the attachment part 5 comprises the patient specific contact surface 51) is shown. The patient specific contact surface 51 in FIG. 2A and FIG. 2B correspond to a part of the diaphysis and also of the epiphysis of the placement bone 206.

Implant 10

The Implant Structure

An implant according to the invention can be in different shapes with or without extending post, having a plate shaped implant body or a more mushroom shaped implant body.

Figure 5A:
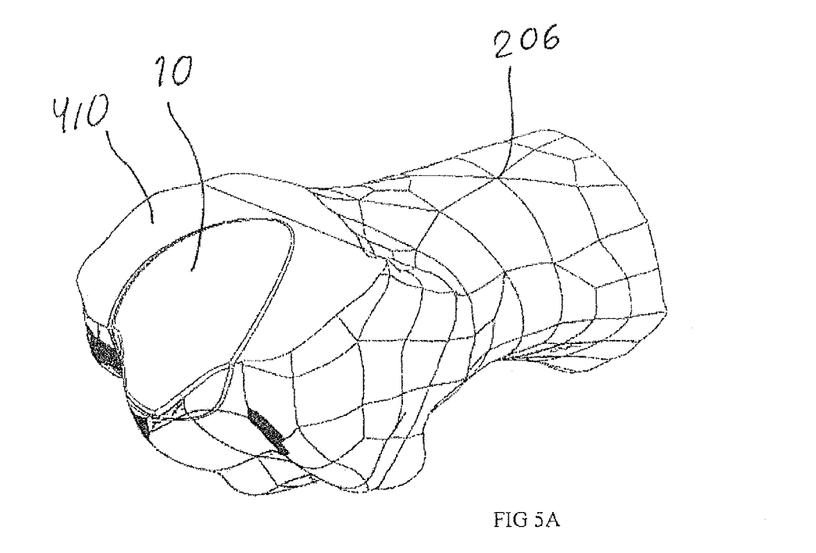
FIGS. 5A and 5B show an exemplifying embodiment of the implant according to the invention after placement in a joint wherein the guide tool is removed and the implant is placed in the joint. The joint is shown in two different angles, obliquely from above in FIG. 5A and from one side in FIG. 5B.
Figure 5B:
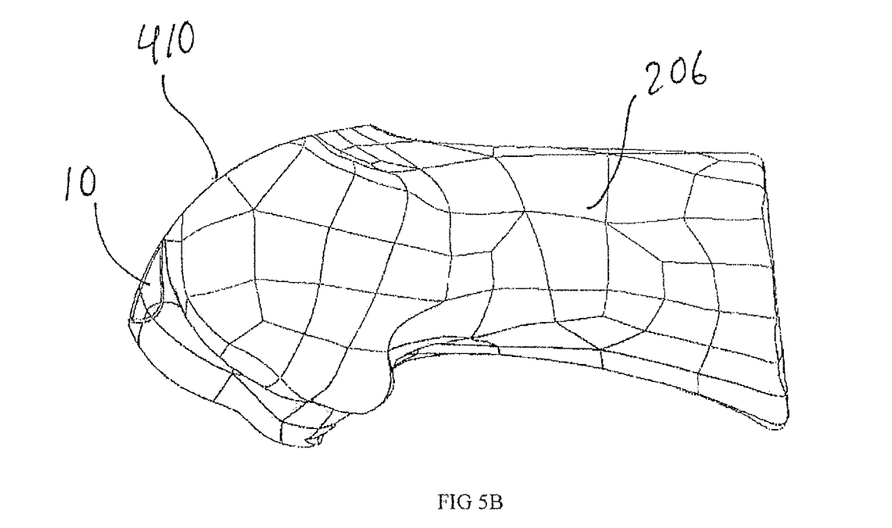

FIGS. 5A and 5B show an example of a medical implant 10 according to the present invention when placed in a joint after surgery. FIG. 4 shows an implant 10 in cross section placed in the joint. The plate shaped implant body 11 has a first surface 16 configured to face the articulating part of the joint and a second surface 21 configured to face bone structure in the joint, the plate shaped implant body 11 has a cross-sectional area that substantially corresponds to the area of the damaged cartilage and the first surface 16 has a curvature that substantially corresponds to the curvature of a healthy articulating surface at the site of diseased cartilage. The extending post 28 extends from the second surface 21. Since the implant 10 of the invention is custom made for a specific patient, FIG. 3 is an exemplifying schematic picture displaying different embodiments of the implant 10. The implant has an articulating first surface 16 and a bone contacting surface, second surface 21 between these surfaces there is a third cartilage contacting surface 19.

The implant is specially designed, depending on the joints appearance and the shape of the damage and in order to resemble the body's own parts, having a surface which corresponds to a three dimensional (3D) image of a simulated healthy joint surface. The implant can be tailor-made to fit each patient's damaged part of the joint.

Implant Body and First Surface

The implant body 11 can be substantially plate shaped or can for example be mushroom shaped having a rounder shape, less flat. By substantially plate shaped is meant that the implant body 11 may be substantially flat or may have a curvature, a 3D curvature of the first surface 16 of the implant body 11 and that allows the borders or the third cartilage contacting surface 19, surrounding the implant body 11 to contact to surrounding joint surface surrounding the implant site. The first surface 16 has the curvature corresponding to a simulated healthy cartilage reconstructed from images taken with MRI image or the CT-scanning of the damaged surface of the joint. Once the implant 10 is placed in the joint there will be a surface with no parts of the implant pointing up from or down below the surrounding cartilage—thus the implant is incorporated to give a smooth surface.

The angle 205 for insertion of the implant in the bone in relation to the longitudinal axis of the placement bone 206 is between 0-45 degrees, preferably between 20-30 degrees. See for example FIG. 4.

The area and the shape of the implant surface 16 is individual depending on the size of cartilage damage and location of the cartilage damage. The area and shape of the implant can be decided by the surgeon himself or be chosen from predetermined shapes. For instance the cross-section of the implant body 11 may have a circular or roughly circular, oval, triangular, square or irregular shape, preferably a shape without sharp edges. The implant head or implant body 11 can vary in size and shape and are adjusted to the size and shape of the damaged cartilage tissue and to the needs of particular treatment situations. The size of the implant 10 may also vary. The surface 16 area of the implant body 11 varies in different realizations of the invention The area of the first surface 16 of the implant varies in different realizations of the invention between 10 $mm^2$-30 $mm^2$ or between 10 $mm^2$-18 $mm^2$.

In general, small implants are preferred since they have a smaller impact on the joint at the site of incision and are also more easily implanted using arthroscopy or smaller open surgical procedures. The primary factor for determining the size of the implant is however the nature of the lesion to be repaired.

The first surface or articulate surface 16 of the implant body 11, and the core of the implant body 11, comprises a biocompatible metal, metal alloy, ceramic material or a polymer. More specifically it can comprise any metal or metal alloy used for structural applications in the human or animal body, such as stainless steel, cobalt-based alloys, chrome-based alloys, titanium-based alloys, pure titanium, zirconium-based alloys, tantalum, niobium and precious metals and their alloys. If a ceramic is used as the biocompatible material, it can be a biocompatible ceramic such as aluminium oxide, silicon nitride or yttria-stabilized zirconia. Preferably the articulate 16 and the core of the implant body 11 may comprise the same or different materials.

The articulate surface 16 may also be further treated on the surface in order to e.g. achieve an even more durable surface or a surface with a lower friction coefficient. Such treatments may include, for example, polishing, heat treatment, precipitation hardening or depositing a suitable surface coating.

The Second Surface 21

The implant body 11 has a bone contact surface (second surface) 21, configured to face or contact the bone structure of the joint. In one embodiment the bone contact surface 21 comprises a biocompatible metal, metal alloy or ceramic, such as any of the metals, metal alloys or ceramic described above for the first surface 16. Preferably the second surface 21 comprises a cobalt chrome alloy (CoCr) or stainless steel.

In one embodiment the bone contact surface 21 comprises, or in one specific embodiment is coated with, a bioactive material or a material that promotes osseointegration and/or bone growth. In an alternative embodiment of the invention the bone contact surface does not comprise a bioactive material and/or is uncoated.

The bioactive material or the material that promotes osseointegration and/or bone growth of, the bone contact surface, if present, preferably stimulates bone to grow into or onto the implant surface. Several such materials that have a stimulating effect on bone growth are known and have been used to promote adherence between implants and bone. Examples of such prior art materials include bioactive glass, bioactive ceramics and biomolecules such as collagens, fibronectin, osteonectin and various growth factors. A commonly used material in the field of implant technology is the ceramic hydroxyapatite (HA), chemical formula $Ca_{10}(PO_4)_6(OH)_2$. HA is the major mineral constituent of bone and is able to slowly bond with bone in vivo. HA coatings have been developed for medical implants to promote bone attachment. Another material commonly used in prior art is bioactive glass. Bioactive glasses, generally comprising $SiO_2$, $CaSiO_3$, $P_2O_5$, $Na_2O$ and/or $CaO$ and possibly other metal oxides or fluorides, are able to stimulate bone growth faster than HA.

In one embodiment the bone contact surface 21 is coated with a double coating. Such double coating may for instance comprise an inner coating comprising titanium (Ti). The second, outer coating, that is configured to contact the cartilage and or bone, is preferably a hydroxyapatite coating. By this design even more long-term fixation of the implant is achieved, since bone in- or on-growth to the implant is further stimulated by the titanium, even if the more brittle hydroxyapatite would eventually shed/dissolve.

The Extending Post 28

The implant replaces an area of damaged cartilage in an articulating surface of a joint. Before the implant is placed in the desired position, the damaged cartilage is removed and also a part of the bone beneath. Furthermore, a hole can be drilled to fit the implant structure.

In one embodiment an extending post of the implant or a rod-part 28 of the implant 10, can be used for securing the implant 10 in the drilled hole of the bone. Such an extending post can be a part of the implant structure or an independent part which may be connected to an implant body. The length of the extending post 28, extending from the implant head, is adjusted to a length needed to secure the implant 10 in the bone. The extending post 28 is intended to give a primary fixation of the implant 10; it provides mechanical attachment of the implant 10 to the bone in immediate connection with the surgical operation.

The position of the extending post 28 on the second surface 21 can be anywhere on the second surface 21 or the extending post 28 may have a central position.

The extending post 28 has a physical structure in the form of for example a cylinder or other shapes such as one or more of a small screw, peg, keel, barb or the like.

The extending post may comprise e.g. a metal, metal alloy or ceramic material, such as the metal, metal alloys or ceramic materials described for the first surface 16 above.

The said extending post 28 can in one embodiment of the invention be coated with a bioactive material with single or double coatings, such as described for the second surface 21 above. In another embodiment of the invention the extending post 28 is uncoated.

Insert Tools

Example of insert tools which may be used inside a guide channel of a guide tool according to the invention is for example a drill guide 300, a punch 302, a hammer tool 304, a reamer bit 306, a drill bit 308, a reamer guide 310, cartilage cutting tool, a cartilage cut drill, a reamer guide etc.

The insert tool is used inside the guide channel of the guide tool and may fit in the guide channel, with a slight tolerance to allow a sliding movement of the insert tool in the guide channel. The insert tool may have a cross-sectional profile that is designed to correspond to the cross-sectional profile of the guide channel 54 with a tolerance enabling the insert tool to slide within the guide channel 54.

Use of Guide Tool

Figure 7A:
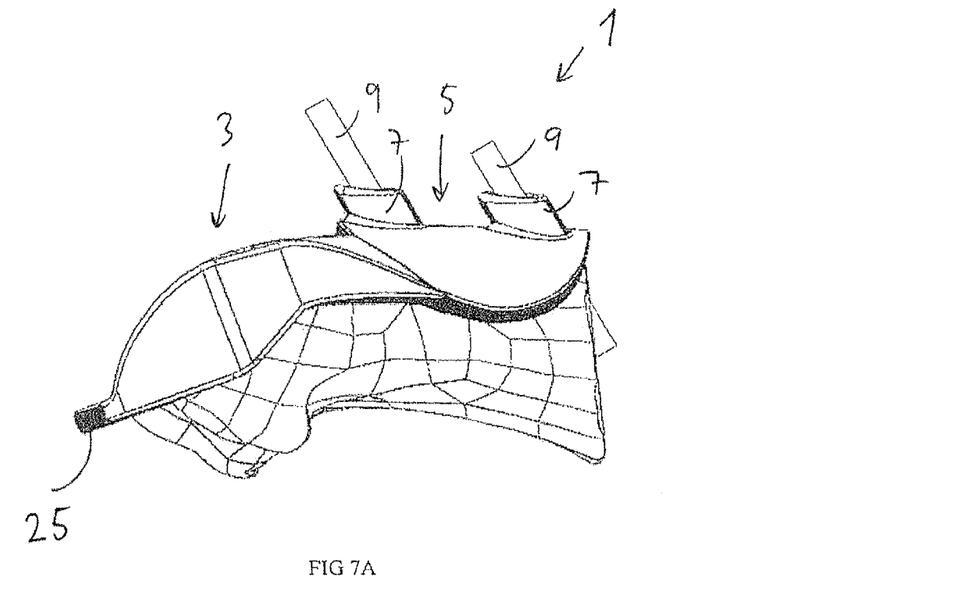
Figure 7B:
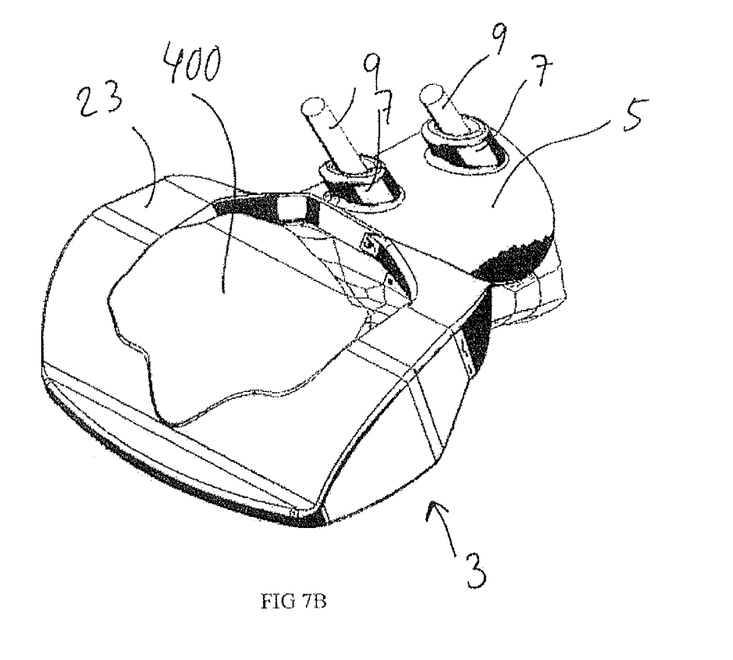

The guide tools and implant and insert tools according to the invention may be used during replacement and or remodeling of damaged bone and/or cartilage in a joint or remodeling of unwanted growth in joint and during insertion of an implant 10 to create a new articulating surface 410 or 400 in a joint, see FIGS. 5A and 7B.

Figure 1B:
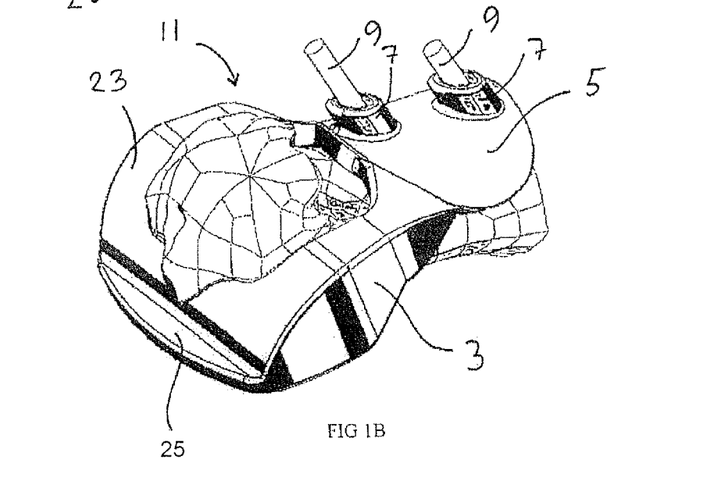

Use of the tools may include the steps of;
Selecting a patient
Determining cartilage damage or changes in cartilage and/or bone structure and/or changes due to arthrosis by collecting or retrieving data and or images using MR or CT scan or by other suitable image collecting method;
Use information (data and/or images) of the cartilage damage and surrounding tissues in order to decide upon planning of the surgery. Planning of surgery may include; deciding placement of customized guide tools during surgery and placement of at least one implant in the joint, determining how to create and/or design guide tools and optionally an implant in the joint depending on the collected data;
Produce the surgical kit of tools, insert tools and at least one guides and optionally implant or implants needed during surgery;
Start surgery by making an opening in the patient so that the patient specific guide tool can be placed in the joint which comprises the cartilage damage;
Placing the a guide tool in the joint, for example in a toe or finger joint, see FIGS. 1A and 1B for an example where a guide tool according to the invention comprising a reamer surface 23 is placed in a toe joint and wherein the area to be remodeled and optionally being replaced by an implant is comprised within the opening 11 and wherein the bone and or cartilage that protrudes 416 above the reamer surface 23 is to be removed by a reamer using the reamer guide surface 23 for guiding and forming a smooth vaulted surface 400 of the cartilage and bone structure beneath. This surface 400 may be used as it is or further replaced by an implant. In FIGS. 1A and 2B the guide tool 1 according to the invention is attached to the diaphysis by contact of the patient specific contact surface 51 of the attachment part 5 (the patient specific contact surface 51 of the attachment part 5 according to the invention is facing the bone 206 and is therefore not seen in the figure) in FIG. 1a-b the attachment part is further attached by using rivets 9 and the guiding device part 3 also comprises a patient specific contact surface (51, dotted lines) contacting the epiphysis part of the placement bone for secure placement of the guide tool 1. In FIG. 7A one example of the invention is shown wherein the attachment part 5 is attached using one rivet 9 and one attachment device 7. FIGS. 1A and 1B show an example according to the invention wherein the patient specific contact surface 51 is actually two separated contact surfaces together achieving robust placement of the guide in the joint.

When the guide tool 1 is placed in the correct (or planned) position, the directing flange 25 of the guide further instructs or directs the surgeon about how to place the guide tool on the surgical site. After reaming, a new surface 400 in the joint is created which will be used for placement of the implant.

After reaming the guide tool comprising the reamer surface 23 is removed from the surgical site the surgical operation is over and the wound is closed or another guide tool 1 is used which comprises a guide channel 54 for guiding insert tools are placed in the joint and attached by contacting the attachment part 5 of the guide tool 1 to a placement bone 206 (proximal phalanxes or metatarsal bones in a toe or the distal-, middle-, or proximal phalanxes or metacarpal bones in a finger).

The second guide tool 1 is then used to guide insert tools for reaming out a planned recess corresponding to the area and or volume and shape of an implant which is to be inserted at the surgical site.

The implant is then inserted in the made recess.

FIGS. 2A and B show an example of a guiding device part 3 which also comprises a patient specific contact surface 51 (not only the attachment part 5 comprises the patient specific contact surface 51. The patient specific contact surface 51 in FIGS. 2A and 2B corresponds to a part of a diaphysis and also of the epiphysis of the placement bone 206 (placement bone 206=proximal phalanxes or metatarsal bones in a toe or the distal-, middle-, or proximal phalanxes or metacarpal bones in a finger).

In FIG. 3 a male part 27 is shown which is placed inside a guide channel 54. Having numbers indicating depth reached by inert tools and wherein the zero point is pointed out for the user by the positioning mark 199 placed in the guide channel 54 (see FIG. 4). FIG. 4 shows a figure when an implant is placed in the recess made by the guide tools according to the invention.

Once the implant 10 is placed in the joint there will be a surface with no parts of the implant pointing up from or down below the surrounding cartilage—the implant is incorporated to give a smooth surface.

Design Method for Designing a Guide Tool

Figure 6:
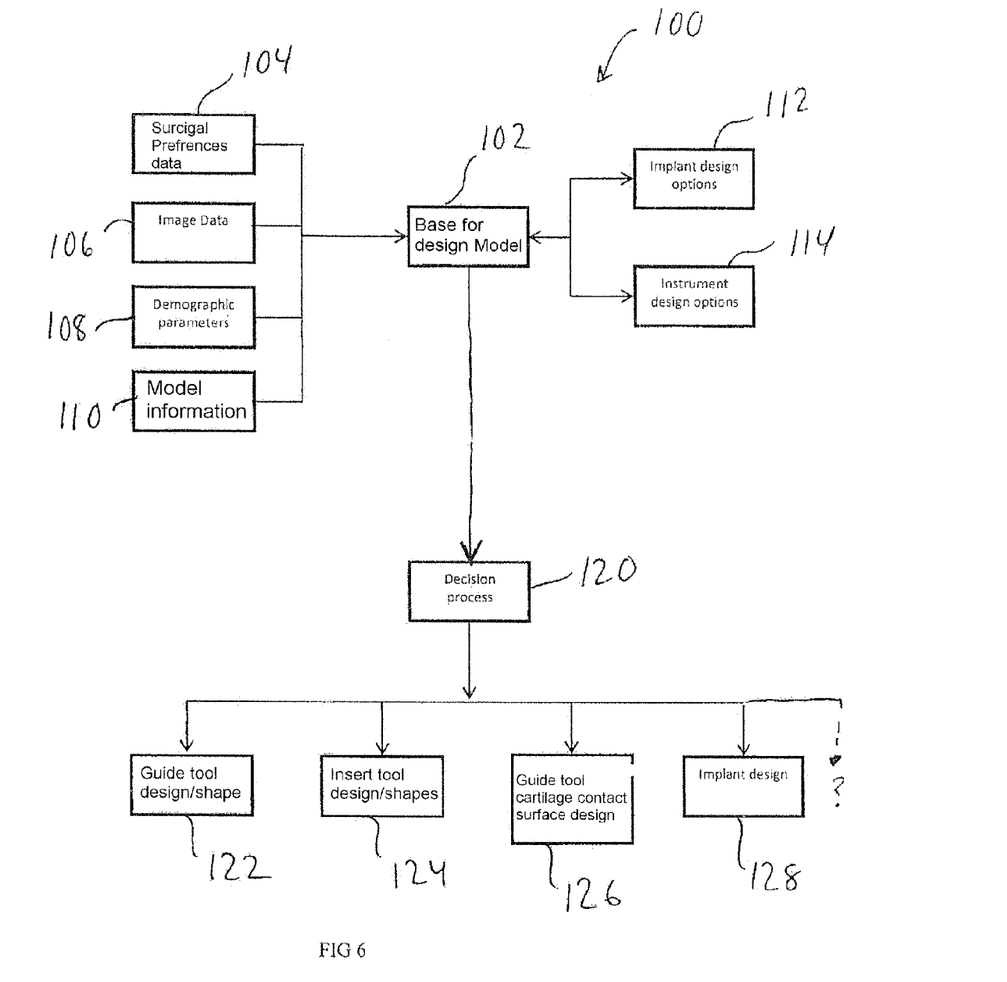
FIG. 6 shows a schematic view over an exemplified embodiment of the design method for designing the guide tool according to the invention.

A design method for customized design of the guide tool or tools and/or insert tools and/or implant according to the invention for a specific patient comprises the steps of;

capturing at least one image data of the patient's toe or finger joints or use image data of a pre captured image of a toe or finger joint and possibly processing said image data using the image data to generate the design of the customized guide tools and/or insert tools and/or implant for use in a surgical procedure to be carried in said toe or finger joint FIG. 6 discloses a schematic flow chart type diagram 100 illustrating inputs and outputs of the various used data sources. Different input data may be provided as base for a design model 102 which is a central decision point where several types of input information is considered and decided upon leading to a decision process 120 which leads to design of the different components of the invention. Examples of output data is Guide tool design/shape 122, insert tool design/shape 124, Guide tool patient specific contact surface design 126, implant design and shape 128 and/or more design parameters needed in order to design a surgical kit according to the invention. See FIG. 6. The production of the designed instrumentation (guide tool, implant, insert tools etc.) may be custom made for the specific patient or selected from available tools on the market. The guide tool and implant is preferably designed to correlate to a specific patient data.

The input data can be selected from but is not limited to;

Surgical preference data 104 indicating at least which toe or finger joint that is to be object for surgery and also which method or surgical approach that is to be used, where the guide is to be placed etc. Further, the surgical preference data 104 also comprise soft tissue information, for example indicating how to relate to interference of soft tissue with design of instrument, allowing customizing the tissue interference.

Image data 106 of the bone and/or cartilage and/or soft tissue of the joint comprising the cartilage or bone damage is also provided to the decision base for the design model 102. Such image data 106 can be obtained by MR or CT scan or by other suitable image collecting methods.

Instrument design options 114 are also added to the base for said design model 102. The instrument design options may depend on type of joint to be repaired, type and location of damage, need of insert tools to be used may also affect instrument design options etc.

The instrument design option data 114 can specify which part or parts of the guide tool that are going to provide the matching patient specific contact surface 51 or surfaces by which the guide tool 1 can be mounted on the patient's body. The instrument design data always comprise input design data of placement of a directing flange 25 somewhere on the guiding device part 3 of the guide tool 1 and also design information about placement of the attachment part 5 so that it corresponds to a patient specific contact surface of the placement bone 206.

Implant design options 112 may for example include shape and size of implant and also decision about angle for insertion of implant in order for the implant 10 achieve long lasting attachment in the joint even if the joint is under pressure. In one embodiment the implant angle is 0-45 degrees or 20-30 degrees in relation to the longitudinal axis of the placement bone 206 in order to achieve good stability and or durability of implantation.

Demographic parameters 108 which are parameters that may relate to the individual patient (age, gender, height, etc.) may also be supplied to give input to the bas for the design model according to the present invention.

Model information 110 for example pre-determined data input which may be relevant for certain illness conditions for the patient etc. and which may be easy to reuse between patients. For example different suitable areas for attachment of an attachment part 5 on a bone surface in a patient suffering from hallux rigidus. Or other predetermined parameters which are useful input for several patients suffering from a similar disease or problem in a joint.

The invention claimed is:

1. A guide tool for at least one of guiding surgical instrumentation, secure positioning, or facilitating insertion of surgical implants for repair of bone or cartilage damage or remodeling of a joint surface for improved mobility in a finger or toe joint, comprising:
    an attachment part comprising a first patient specific contact surface adapted to fit proximal phalanxes or metatarsal bones in a toe or distal-, middle-, or proximal phalanxes or metacarpal bones in a finger;
    a directing flange placed on a second patient specific contact surface opposite the first patient specific contact surface; and
    a reamer guide surface arranged for guiding a reamer in a certain predetermined angle to remove at least one of bone or cartilage in such a way that a remodeled smooth vaulted surface is formed.

2. The guide tool according to claim 1, wherein the attachment part further comprises a portion of the first patient specific contact surface which is adapted to correspond to a part of a contour and shape of a joint surface of a diaphysis or long shaft part of the proximal phalanxes or metatarsal bones in a toe or the distal-, middle-, or proximal phalanxes or metacarpal bones in a finger.

3. The guide tool according to claim 1, wherein the attachment part further comprises:
    a first area of the first patient specific contact surface which is adapted to correspond to a bone surface of a diaphysis which is a long shaft part of the proximal phalanxes or metatarsal bones in a toe or the distal-, middle-, or proximal phalanxes or metacarpal bones in a finger; and
    a second area of the first patient specific contact surface comprised in at least one of the structure of a guide device part or the directing flange of the guide tool, wherein said second area of the patient specific contact surface is adapted to correspond to a surface of an epiphysis which is an expanded portion of the proximal phalanxes or metatarsal bones in a toe or the distal-, middle-, or proximal phalanxes or metacarpal bones in a finger.

4. The guide tool according to claim 1, further comprising a guiding device part and an opening comprised in the guiding device part of the guide tool.

5. The guide tool according to claim 1, further comprising an attachment device.

6. The guide tool according to claim 1, wherein the guide tool is made of materials approved for medical procedures selected from the group consisting of ceramic, polymer, and metal material.

7. The guide tool according to claim 1, further comprising a guiding device part, wherein the guiding device part comprises an opening arranged to face a part of the finger joint or the toe joint which has joint damage.

8. The guide tool according to claim 1, further comprising a guiding device part, wherein the directing flange comprises a body which is a protuberance on the guiding device part.

9. The guide tool according to claim 1, further comprising a guiding device part, wherein the directing flange is a small protrusion of irregular shape or any other suitable shape giving support in placement located on the guiding device part.

10. The guide tool according to claim 9, wherein the directing flange is arranged to point in a direction so that the directing flange is capable of enclosing a shape of the bone or the cartilage or both the bone and the cartilage in the toe joint or the finger joint.

11. The guide tool according to claim 1, further comprising an opening arranged to follow or match a shape of a joint surface beneath which the guide tool can be placed so as to indicate desired placement of the guide tool and to make the guide tool less prone to move during surgery.

12. A design method, comprising designing shape and design of the guide tool according to claim 1.

13. A method comprising repairing a joint damage in a joint or remodeling of a joint surface using the guide tool according to claim 1 and insert tools.

14. A method comprising remodeling a joint surface without inserting an implant using the guide tool according to claim 1.

15. A method comprising remodeling a joint surface using the guide tool according to claim 1, and then using a second guide tool for repair of a joint damage and insertion of an implant.

16. A design method comprising:
collecting input data selected from the group consisting of surgical preference data, image data, demographic parameters, model information, implant design options, and instrument design options;
considering all collected data and transferring the data to form a decision process; and
using the decision process to make output data comprising shape and design of at least one of a guide tool, shape and design of insert tools, shape and design of guide tool patient specific contact surface, or implant design,
wherein the input data comprises data for designing a patient specific contact surface of the guide tool adapted to fit a patient specific contact surface of proximal phalanxes or metatarsal bones in a toe or distal-, middle-, or proximal phalanxes or metacarpal bones in a finger, and
wherein the output data comprises shape and design of a reamer guide surface of the guide tool arranged for guiding a reamer in a certain predetermined angle to remove at least one of bone or cartilage in such a way that a remodeled smooth vaulted surface is formed.

17. The design method according to claim 16, wherein the input data further comprises designing another area of the patient specific contact surface of the guide tool adapted to fit at least a part of a diaphysis or a long shaft part of a placement bone.

* * * * *